United States Patent [19]

Earl et al.

[11] Patent Number: 5,087,628

[45] Date of Patent: Feb. 11, 1992

[54] 4,4'-[9H-FLUOREN-9-YLIDENEBIS(METHYLENE)]BISPYRIMIDINE FOR TREATING NEUROLOGICAL DISORDERS

[75] Inventors: Richard A. Earl, Wilmington; Victor J. DeNoble, Newark, both of Del.

[73] Assignee: Du Pont Merck Pharmaceutical Company, Wilmington, Del.

[21] Appl. No.: 464,433

[22] Filed: Jan. 12, 1990

[51] Int. Cl.$^5$ .................. A61K 31/505; C07D 239/26
[52] U.S. Cl. ..................................... 514/256; 544/294
[58] Field of Search ........................ 544/294; 514/256

[56] References Cited

U.S. PATENT DOCUMENTS 4,760,083  7/1988  Myers et al. .................. 546/256

OTHER PUBLICATIONS

Earl, et al., C. A. 111:153,640u, (1989), vol. 111.

Primary Examiner—Joseph Paul Brust

[57] ABSTRACT

A fluorene compound, 4,4'-[9H-fluoren-9-ylidenebis(methylene)]bispyrimidine, or a pharmaceutically acceptable salt thereof is useful in treating various neurological disorders in mammals. This compound has efficacy over a broad dosage range as measured by hypoxia induced cognition impairment and has a wide safety margin as measured by the ratio of cognition to the onset of overt symptoms.

3 Claims, No Drawings

4,4'-[9H-FLUOREN-9-YLIDENEBIS (METHYLENE)]BISPYRIMIDINE FOR TREATING NEUROLOGICAL DISORDERS

BACKGROUND OF THE INVENTION

1. Field of the Invention

This invention relates to 4,4'-[9H-fluoren-9-ylidenebis(methylene)]bispyrimidines, pharmaceutical compositions containing them and methods of using them to treat neurological disorders in mammals.

2. State of the Art

Alzheimer's Disease (AD) and Senile Dementia (SD) are neurological disorders generally characterized by a reduction in cortical cholinergic activity. Neurological disorders may be characterized by altered neurotransmitter function and concomitant cognitive impairment in diseases such as, but not limited to, Alzheimer's Disease, Parkinson's Disease, Pick's Disease, Huntington's Disease, and Age Associated Memory Impairment. This had led to a focus on the basal forebrain cholinergic system as the major source of neurochemical and neuroanatomical substrates mediating age-related memory loss. However, it is very unlikely, given the complexity of the brain, that any single neurotransmitter would selectively and exclusively be involved in a neurological disorder so pervasive as dementia or age-related memory impairment. A growing literature has described multiple neurotransmitter, neuroanatomical and behavioral changes in dementia from varying etiologies It is, therefore, possible and likely that age-related memory deficits and cognitive impairment resulting from AD or SD involve concurrent changes in several neurotransmitter systems and neurotransmitters replacement therapy should involve multiple systems in the brain.

3. Information Disclosure

U.S. Pat. No. 4,760,083, issued July 26, 1988, and coassigned application Ser. No. 07/234,382, filed Aug. 23, 1988, (EP-A-311,010, Apr. 12, 1989), describe many compounds useful in the treatment of neurological disorders such as Alzheimer's Disease and Senile Dementia. In EP-A-311,010, certain 4,4'-[9H-fluoren-9-ylidenebis(methylene)]bispyridyl compounds are specifically disclosed as being useful in the treatment of neurological disorders. While the compound of the present invention is within the broad scope of Ser. No. 07/234,382, there is no suggestion that this compound has an unexpectedly good dosage profile as measured by hypoxia induced cognition impairment and a good safety margin.

SUMMARY OF THE INVENTION

According to the present invention there is provided 4,4'-[9H-fluoren-9-ylidenebis(methylene)]bispyrimidine, or a pharmaceutically acceptable salt thereof.

Also provided are pharmaceutical compositions containing the aforesaid compound and methods of using them to treat neurological disorders.

DETAILED DESCRIPTION OF THE INVENTION 4,4'-9H-fluoren-9-ylidenebis(methylene)]bispyrimidine can be prepared by any of the general synthesis procedures described in EP-A-311,010 starting with fluorene. In particular the compound is prepared by the reaction of fluorene with 4-chloromethylpyrimidine.

In the following Example, parts and percentages are by weight unless otherwise indicated.

EXAMPLE 1

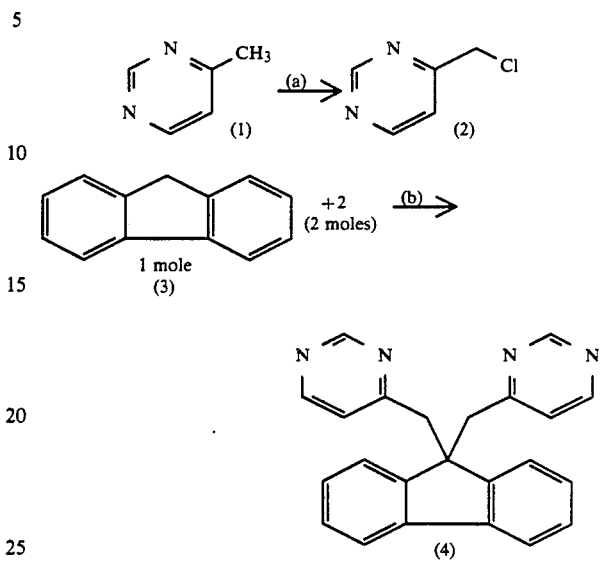

Step (a): To a mixture of 4-methylpyrimidine (120 mmol, 11.29 g, (1)) and N-chlorosuccinimide (150 mmol, 20.03 g) in carbon tetrachloride (500 ml) was added benzoyl peroxide (1.5 g, 6.2 mmol). The reaction mixture was heated at reflux for 8 hrs, then allowed to cool to room temperature overnight. The mixture was filtered through a thin pad of Celite ® to remove the succinimide by-product. The product (2) was extracted into 3N HCl (3×100 ml). The combined acid layers were basified with 50% NaOH solution, and the product was extracted into dichloromethane (5×100 ml). The product was further purified via a silica gel column (500 g, EM Reagents #9385), eluting with ether. The components of the reaction mixture eluted in the following order, as analyzed by TLC (EM Reagents #15327): 4-($\alpha,\alpha$-dichloromethyl)pyrimidine, $R_f$ 0.43; product (2), $R_f$ 0.35; starting material (1), $R_f$ 0.16. $^1$H-NMR(CDCl$_3$) of product (2) δ4.64 (s, 2); 7.57 (d, 1, J=5.2Hz), 8.80 (d, 1, J=5.2Hz), 9.19 (s, 1). Yield —6.22 g, 40%.

Step (b): Into a 3-necked flask equipped with two addition funnels and nitrogen inlet was added fluorene ((3), 24 mmol, 4.0 g) and tetrahydrofuran (THF) (200 ml). In one addition funnel was placed (2) (6.22 g, 48 mmol) dissolved in 90 ml THF. Potassium bis(trimethylsilyl)amide (0.5M in toluene, 48 mmol, 96 ml) was placed in the second addition funnel. While stirring the contents of the reaction flask at room temperature, the contents of the addition funnels were added concurrently in a dropwise fashion. After addition was complete, the solution was stirred for an additional 2 hrs. 100 ml 3N HCl was added, the organic layer was diluted with ethyl acetate, and the layers were separated. The product was extracted into 3N HCl (3×100 ml). The combined acidic layers were basified with 50% aq. NaOH, and the product was extracted into chloroform. The solution was dried over magnesium sulfate, filtered, and evaporated to a solid. After chromatography on silica gel using 10% methanol/ethyl acetate, the product was recrystallized from dichloromethane/hexane to give off-white crystals of final product (4). Yield —4.6 g, 55%, mp 143°–145° C. $^1$H-NMR (CDCl$_3$) δ3.63 (s, 4H); 6.34 (dd, 2H, J=1, 5Hz); 7.34 (m, 4H); 7.50 (m, 4H); 8.19 (d, 2H, J=5Hz); 8.55 (s, 2H). Mass spec. 350 (M+). IR (KBr) 1581, 1545, 1475, 1450, 1387, 738 cm$^{-1}$. Analysis: Calc. for $C_{23}H_{18}N_4$: C, 78.83; H, 5.18; N, 15.99. Found: C, 78.91; H, 5.41; N, 16.00.

UTILITY

In Vitro Studies

Biochemical Test Procedure

The effect of the compound of Example 1 on the release of acetylcholine (ACh) from rat cerebral cortex slices was tested essentially using a slice superfusion procedure described by Mulder et al., Brain Res., 70, 372, (1974), as modified according to Nickolson et al, Naunyn Schmied. Arch. Pharmacol., 319, 48 (1982).

Male Wistar rats (Charles River) weighing 175-200 grams were used. They were housed for at least seven days before the experiment in the animal facility under a 12-12 hour light/dark cycle (light on 6.00h, light off 18.00h). They had ad lib access to standard rat chow (Purina) and deionized water.

Rats were decapitated and brains were dissected immediately. Slices (0.3 mm thick) from the parietal cortex were prepared manually using a recessed Lucite® guide and subsequently cut into 0.25×0.25 mm squares.

Slices (approximately 100 mg net weight) were incubated in 10 ml Krebs-Ringer (KR) medium containing (mM): NaCl (116), KCl (3), $CaCl_2$ (1.3), $MgCl_2$ (1.2), $KH_2PO_4$ (1.2), $Na_2SO_4$ (1.2), $NaHCO_3$ (25), glucose (11), to which 10 μCi $^3$H-Choline (spec. act approx 35 Ci/mmol; NEN) and 10 nmoles unlabelled choline had been added to give a final Concentration of $10^{-6}$M. Incubation was carried out for 30 minutes at 37° C. under a steady flow of 95% $O_2$/5% $CO_2$. Under these conditions, part of the radioactive choline taken up was converted into radioactive ACh by cholinergic nerve endings, stored in synaptic vesicles and released upon depolarization by high-K+-containing media.

After labelling of the ACh stores, the slices were washed 3 times with non-radioactive KR-medium and transferred to a superfusion apparatus to measure the drug effects on ACh release. The superfusion apparatus consisted of 10 thermostated glass columns of 5 mm diameter which were provided with GF/F glass fiber filters to support the slices (approximately 10 mg tissue/column). Superfusion was carried out with KR-medium (0.3 ml/min) containing $10^{-5}$M hemicholinium-3 (HC-3). HC-3 prevents the uptake of choline, formed during the superfusion from phospholipids and released ACh, which would be converted into unlabelled ACh, and released in preference to the preformed, labelled ACh. The medium was delivered by a 25-channel peristaltic pump (Ismatec; Brinkman) and was warmed to 37° C. in a thermostated stainless steel coil before entering the superfusion column. Each column was provided with a 4-way slider valve (Beckman Instruments) which allowed rapid change of low-to high-K+-KR-medium and with two 10-channel, 3-way valves which were used to change from drug-free to drug-containing low-and high-K+-KR-medium.

After 15 minutes washout of non-specifically bound radioactivity, the collection of 4 minute fractions was started. After 3 four-min. collections, the KR medium was changed for KR medium of which the KCl concentration had been increased to 25 mM (high-K+-KR-medium) (S1). Depolarization-induced stimulation of release by high-K+-KR-medium lasted for 4 minutes. Drug free low-and high-K+-KR-medium were then substituted by drug- or vehicle-containing low-and high-K+-KR-medium and superfusion was continued for 3 four-min. collections with low-K+-KR-medium, 1 four-min. collection with high-K+-KR-medium (S2) and 2 four-min. collections with low K+-KR-medium. Drug was added to the media by 100-fold dilution of appropriate concentrations of the drug (in 0.9% NaCl/-$H_2O$) with either low- or high-K+-KR-medium. All superfusion fractions were collected in liquid scintillation counting vials. After superfusion, the slices were removed from the superfusion columns and extracted in 1.0 ml of 0.1N HCl. To superfusion fractions and extracts 12 ml Liquiscint ® counting fluid (NEN) was then added and samples were counted in a Packard Tricarb Liquid Scintillation Counter. No corrections were made for quenching.

The ratio of S2/S1 (as compared to controls where no drug was present during S2) was a measure of the ability of the drug to enhance or depress stimulus-induced acetylcholine release.

The in vitro ACh release data is summarized in Table I.

TABLE I

| % INCREASE OF STIMULUS-INDUCED ACh RELEASE IN RAT CEREBRAL CORTEX IN VITRO | | | |
|---|---|---|---|
| Example | $10^{-6}$ | $10^{-5}$ | $10^{-4}$ (M) |
| 1 | 109 | 142 | 205 |

Hypoxia-Induced Amnesia

Effects of the Compound of Example 1 on Cognitive Performance in the Rat

The compound of Example 1 was tested in a model of hypoxia-induced amnesia in rats. In this model, (passive avoidance, PA) the ability of a rat to remember (retention latency) is decreased by pretraining exposure to a hypoxic environment containing reduced oxygen concentrations.

Median PA response retention latencies of rats exposed to normal air (21% oxygen) or moderate hypoxia (9-10% oxygen) were at the maximal level of 300 sec. However, when the oxygen concentration was reduced to 7%, or 6.5% oxygen, PA retention latencies were reduced to 167, 130, and 43 sec, respectively demonstrating a significant and reliable amnesia for the task. A 6.5% oxygen concentration was selected for its ability to produce maximal memory deficit without mortality.

The compound of Example 1 protected against the hypoxia-induced amnesia when administered one minute after training at doses ranging from 0.005 to 0.3 mg/kg s.c. The median retention latencies were significantly greater than vehicle control, (p<0.025) resulting in a prevention of the experimentally-induced amnesia. The peak effective dose range (PEDR) was observed to be the 0.01 to 0.1 mg/kg s.c. dose with the retention latency reaching 181.0 sec. At a dose of 1 mg/kg, the retention latency was not significantly different from vehicle alone.

Subcutaneous administration at 0.05-0.3 mg/kg also protected against hypoxia-induced amnesia when administered prior to (35 min before) PA training. Median retention latencies increased from 19 sec in vehicle treated rats to 150.5, 161, and 51.5 sec in rats dosed with 0.05, 0.10 and 0.30 mg/kg p.o. respectively. In summary, the compound of Example 1 given subcutaneously protected against hypoxia-induced memory deficit using a single trial passive avoidance procedure over a dose range of 0.005–0.3 mg/kg s.c. with a peak effect dose of 0.01 mg/kg.

Oral administration of the compound of Example 1 at 0.05–0.3 mg/kg also protected against hypoxia-induced amnesia when administered prior to (35 min. before) PA training.

The compound of Example 1 was administered orally to rats at doses ranging from 50–400 mg/kg. Groups of 5 rats were administered the compound and observed for the presence of overt symptoms from 15 min to 6 hr. Mortality was scored at 24 hr. also. The range of doses tested were 0, 50, 100, 200 and 400 mg/kg p.o. and 0, 2.5, 5, 10, 50, 100, 200, and 400 mg/kg s.c. It produced mortality at 400 mg/kg. No other symptoms were observed. Subcutaneously, the compound of Example 1 was administered at doses ranging from 2.5 to 400 mg/kg. It produced loss of the lift reflex at 5.0 mg/kg but not at higher doses. No other overt symptoms were observed. The compound of Example 1 has a very high safety margin in that in the rat at high doses, the main symptoms were tremor and mortality, both occurring at 4000 to 40000 times the peak effective dose range (PEDR) of 0.01 to 0.1 mg/kg sc.

The foregoing test results suggest that the compound of this invention has utility in the treatment of neurological disorders in patients, with a wide safety margin. The compound of this invention can be administered to treat said disorders by any means that produces contact of the active agent with the agent's site of action in the body of a mammal. The compound can be administered by any conventional means available for use in conjunction with pharmaceuticals, either as an individual therapeutic agent or in a combination of therapeutic agent. It can be administered alone, but is generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. For use in the treatment of said diseases, a daily oral dosage of active ingredient can be about 0.001 to 50 mg/kg of body weight. Ordinarily a dose of 0.01 to 10 mg/kg per day in divided doses one to four times a day or in sustained release form was effective to obtain the desired results.

Dosage forms (compositions) suitable for administration contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, 9, Osol, a standard reference text in this field.

Formulations for subcutaneous administration can be prepared essentially as described in *Remington's Pharmaceutical Sciences*. These formulations usually consist predominantly of a liquid vehicle, the active drug, and excipients. The liquid vehicle can be essentially aqueous, for example, water and sodium chloride or dextrose to adjust the tonicity; water miscible vehicles, such as ethanol, polyethylene glycol, and propylene glycol; or nonaqueous vehicles consisting of water-immiscible oils such as ethyl oleate, isopropyl myristate, and benzyl benzoate. Aqueous and water-immiscible vehicles can be combined in the presence of suitable surfactants to form emulsions. Commonly used excipients include solubilizing agents, buffers, antioxidants, chelating agents, antimicrobial agents, suspending agents, and agents to affect viscosity. In addition to these essentially liquid preparations, it is sometimes desirable to prepare a formulation which can be effective over prolonged periods of time. This can be accomplished by incorporation of the drug into a solid polymeric mass, which can be prepared as pellets or as a single matrix. All of these agents must fulfill the requirements of sterility and absence of pyrogenicity.

Useful pharmaceutical dosage-forms for administration of the compound of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

What is claimed is:

1. 4,4'-[9H-fluoren-9-ylidenebis(methylene)]-bispyrimidine, or a pharmaceutically acceptable salt thereof.

2. A pharmaceutical composition consisting essentially of a pharmaceutically suitable carrier and an effective amount of the compound of claim 1.

3. A method of treating a cognitive or neurological dysfunction in a mammal comprising: administering to the mammal an effective amount of the compound of claim 1.

* * * * *